United States Patent [19]

Zaiger

[11] Plant 5,228

[45] May 8, 1984

[54] NECTARINE TREE—2W68C

[76] Inventor: Chris F. Zaiger, 537 Rosemore Ave., Modesto, Calif. 95351

[21] Appl. No.: 439,223

[22] Filed: Dec. 13, 1982

[51] Int. Cl.[3] ..... A01H 5/03

[52] U.S. Cl. ..... Plt./41

[58] Field of Search ..... Plt./41

*Primary Examiner*—Robert E. Bagwill

[57] ABSTRACT

A new and distinct variety of nectarine tree which is of large size with upright vigorous growth; the tree being a regular and productive bearer of large, firm, yellow flesh clingstone fruit having yellow skin color substantially overspread with red and having excellent eating and shipping quality, maturing 3 to 4 days later than Zee Gold nectarine (U.S. Plant Pat. No. 3,087).

1 Drawing Figure

ORIGIN OF THE VARIETY

The new variety was originated by me in my experimental orchard at Modesto, Calif. The nectarine tree was a selection of a second generation seedling from a cross between Zee Gold nectarine, (U.S. Plant Pat. No. 3,087) and Early Sun Grand nectarine, (U.S. Plant Pat. No. 1,420). I selected the seedling from a large group of seedlings that were grown and maintained under close observation by me and the present variety which evidenced distinctive desirable characteristics was selected for asexual reproduction and commercialization.

SUMMARY OF THE VARIETY

My new and distinct variety of nectarine tree is of large size, upright vigorous growth and a regular and productive bearer of large, firm, yellow flesh, clingstone fruit with excellent eating quality and the ability to ship to long distance markets. The fruit is further characterized by being larger and maturing 3 to 4 days later than Zee Gold nectarine (U.S. Plant Pat. No. 3,087).

BRIEF DESCRIPTION OF THE DRAWING

The accompanying photographic illustrations show typical specimens of the foliage and fruit of my new variety of nectarine tree, with an exterior and sectional view of the fruit with the stone in place and a section of branch and foliage with the upper and lower surface of the leaves being illustrated. The photographs were taken shortly after being picked at maturity (shipping ripe) and the colors are as nearly true as is reasonably possible in a color representation of this type.

DESCRIPTION OF THE VARIETY

The following is a detailed description of the foliage and fruit of my new nectarine variety, as based on observations of specimens grown at Modesto, Calif., with color terminology in accordance with Reinhold Color Atlas by A. Kornerup and J. H. Wanscher.

Tree:
- *Size.*—Large.
- *Vigor.*—Vigorous.
- *Form.*—Upright.
- *Productivity.*—Productive.
- *Bearer.*—Regular.

Trunk:
- *Size.*—Medium stocky.

- *Texture.*—Medium shaggy.
- *Color.*—Brownish gray.

Branches:
- *Size.*—Medium stocky.
- *Texture.*—Smooth to medium rough.
- *Color.*—Brown to grayish brown.
- *Lenticels.*—Medium size. Medium quantity.

Leaves:
- *Size.*—Large. Average length — 6½". Average width — 1⅝".
- *Form.*—Lanceolate. Acutely pointed.
- *Texture.*—Smooth.
- *Margin.*—Crenate.
- *Petiole.*—Average length — ⅝. Average width — 1/16".
- *Glands.*—Number 2 to 4, usually 2. Globose. Positioned on lower part of leaf blade and upper part of petiole.
- *Color.*—Upper surface — deep green (28-E-5) to (28-F-6). Lower surface — grayish green (28-D-5) to (28-D-7).

Flower buds:
- *Size.*—Medium to large.
- *Form.*—Plump.
- *Pubescence.*—Pubescent.

Flowers:
- *Size.*—Large — showy.
- *Blooming period.*—Feb. 26, 1982 to Mar. 8, 1982. Varies slightly with climatic conditions.
- *Pollen.*—Present.
- *Color.*—Pink.

Fruit:
- *Maturity when described.*—Hard ripe.
- *Date of first picking.*—June 5, 1981.
- *Date of last picking.*—June 11, 1981.
- *Size.*—Large. Average diameter axially — 2 7/16 to 2¾". Average transversely in suture plane 2 7/16 to 2¾".
- *Form.*—Nearly globose — slightly larger on one side.
- *Suture*—Shallow — extends from apex to base.
- *Ventral surface.*—Usually rounded, varies from equal to unequal.
- *Cavity.*—Rounded to slightly elongated. Average depth — 5/16". Average breadth — 5/16".
- *Base.*—Retuse.
- *Apex.*—Short — slightly rounded.

Skin:
- *Thickness.*—Medium.

*Texture.*—Medium — tenacious to flesh.
*Tendency to Crack.*—None.
*Down.*—Wanting.
*Color.*—Yellow ground color (5-A-7) to (5-B-8). Overspread with red (8-A-8) to (9-B-8).

Flesh:
*Color.*—Dark yellow (4-A-7) to (4-A-8) to Cadmium orange (5-A-7) to (5-A-8).
*Juice.*—Moderate.
*Texture.*—Firm.
*Fibers.*—Few — tender.
*Amygdalin.*—Wanting.
*Ripens.*—Evenly.
*Flavor.*—Mild.
*Aroma.*—Very little.
*Eating quality.*—Excellent.

Stone:
*Type.*—Clingstone.
*Size.*—Large. Average length — 1½". Average width — 1⅛". Average thickness — ⅝".
*Form.*—Ovoid.
*Base.*—Mostly straight.
*Apex.*—Acuminate.
*Sides.*—Mostly equal.

*Surface.*—Furrowed toward apex and pitted toward base.
*Ridges.*—Rounded toward apex.
*Tendency to split.*—Slight.
*Color.*—Light brown (8-C-5) to (8-D-6).

Use: Local and long distance markets. Dessert.
Keeping quality: Exellent.
Shipping quality: Excellent.

The nectarine tree and its fruit herein decribed as grown by me at Modesto, Calif. may vary in slight detail due to different climatic, soil conditions and cultural practices.

I claim:

1. A new and distinct variety of nectarine tree of large size, upright growth and a regular and productive bearer of large, yellow flesh, clingstone fruit with excellent eating and shipping quality and the tree is further characterized by the uniform distribution of large size fruit throughout the tree with relatively uniform ripening of the fruit, ripening 3 to 4 days later than Zee Gold nectarine (U.S. Plant Pat. No. 3,087).

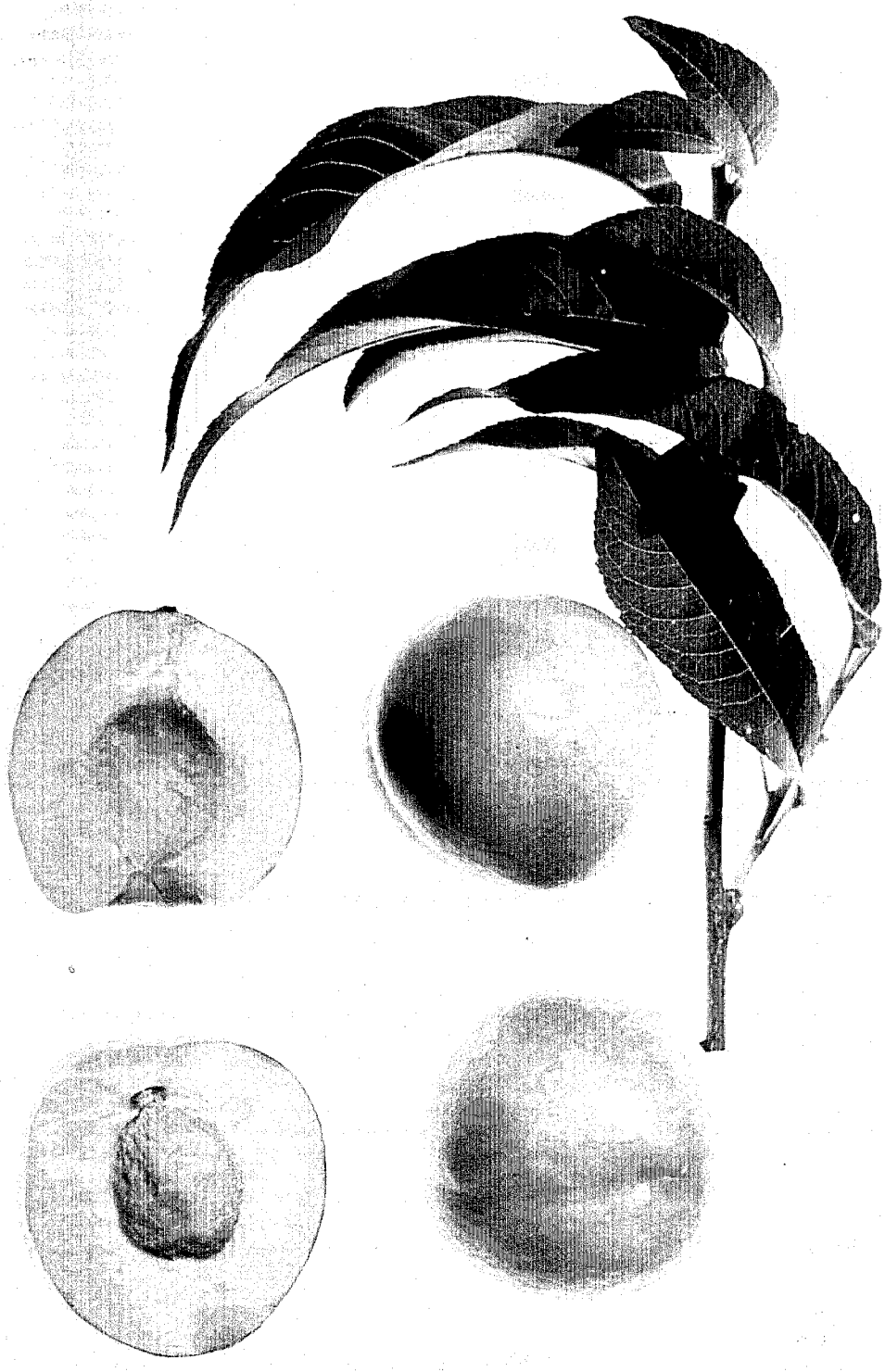

* * * * *